(12) United States Patent
Ujihara et al.

(10) Patent No.: US 6,225,495 B1
(45) Date of Patent: May 1, 2001

(54) ESTER COMPOUNDS

(75) Inventors: Kazuya Ujihara, Yokohama; Tomonori Iwasaki, Sanda, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/256,095

(22) Filed: Feb. 24, 1999

(30) Foreign Application Priority Data

Feb. 26, 1998 (JP) .................................................. 10-045004

(51) Int. Cl.[7] .................................................... C07C 69/74
(52) U.S. Cl. ............................................ 560/124; 514/531
(58) Field of Search .............................. 560/124; 514/531

(56) References Cited

U.S. PATENT DOCUMENTS

| | | |
|---|---|---|
| 3,835,220 | 9/1974 | Matsui et al. . |
| 4,024,163 | 5/1977 | Elliottt et al. . |
| 4,183,950 | 1/1980 | Naumann et al. . |
| 4,370,346 | 1/1983 | Punja . |
| 4,376,786 | 3/1983 | Maurer et al. . |
| 4,405,640 | 9/1983 | Punja . |

FOREIGN PATENT DOCUMENTS

| | | |
|---|---|---|
| 0061053A1 | 9/1982 | (EP) . |
| 2327883A | 2/1999 | (GB) . |
| 47-43333 | 12/1972 | (JP) . |

OTHER PUBLICATIONS

L. Crombie et al, J. Chem. Soc. (C), 1970, pp. 1076–1080.
Database WPI, XP002104367, Feb. 9, 1993.

*Primary Examiner*—Paul J. Killos
(74) *Attorney, Agent, or Firm*—Birch, Stewart, Kolasch & Birch, LLP

(57) ABSTRACT

Ester compounds shown by the formula:

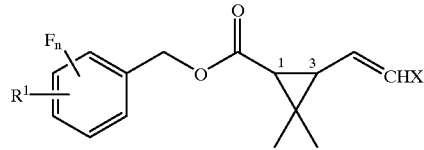

wherein $R^1$ represents a hydrogen atom, halogen atom, $C_1$–$C_3$ alkyl group optionally substituted by halogen atom(s), $C_2$–$C_3$ alkenyl group optionally substituted by halogen atom(s), $C_1$–$C_3$ alkoxy group optionally substituted by halogen atom(s), $C_1$–$C_3$ alkylthio group optionally substituted by halogen atom(s) or ($C_1$–$C_3$ alkoxy)methyl group optionally substituted by halogen atom(s), n represents an integer of 1 to 4 and X represents a hydrogen atom or $C_1$–$C_3$ alkyl group, have excellent pesticidal activity.

19 Claims, No Drawings

ESTER COMPOUNDS

The present invention relates to ester compounds and pesticides containing thereof as an active ingredient.

Japanese Patent Publications describe some ester compounds such as (4-allylphenyl)methyl 1RS-trans-2,2-dimethyl-3-((E)-1-propenyl)cyclopropanecarboxylate in JP-sho-47-43333A and (2,3,5,6-tetrafluorophenyl)methyl (1R)-trans-2,2-dimethyl-3-(2-methyl-1-propenyl) cyclopropanecarboxylate in JP-hei-5-32509A. However, these ester compounds are not satisfactorily effective. The problem of the present invention is to provide a compound having an excellent pesticidal activity.

The present invention provides an ester compound (hereinafter referred to as "the present compound") shown by the formula (I):

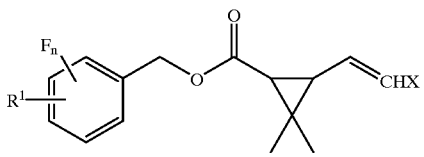

wherein $R^1$ represents a hydrogen atom, halogen atom, $C_1$–$C_3$ alkyl group optionally substituted by halogen atom(s), $C_2$–$C_3$ alkenyl group optionally substituted by halogen atom(s), $C_1$–$C_3$ alkoxy group optionally substituted by halogen atom(s), $C_1$–$C_3$ alkylthio group optionally substituted by halogen atom(s) or ($C_1$–$C_3$ alkoxy)methyl group optionally substituted by halogen atom(s), n represents an integer of 1 to 4 and X represents a hydrogen atom or $C_1$–$C_3$ alkyl group, and a pesticide containing thereof as an active ingredient.

The halogen atoms in the present invention are exemplified by a fluorine atom, chlorine atom, bromine atom; the $C_1$–$C_3$ alkyl group optionally substituted by halogen atom(s) is exemplified by a methyl group, ethyl group, trifluoromethyl group; the $C_2$–$C_3$ alkenyl group optionally substituted by halogen atom(s) is exemplified by an allyl group, 2,2-dichlorovinyl group; the $C_1$–$C_3$ alkoxy group optionally substituted by halogen atom(s) is exemplified by a methoxy group, trifluoromethoxy group; the $C_1$–$C_3$ alkylthio group optionally substituted by halogen atom(s) is exemplified by a methylthio group; and the ($C_1$–$C_3$ alkoxy)methyl group optionally substituted by halogen atom(s) is exemplified by a methoxymethyl group.

The present compounds can be produced by the following methods.

(Method A)

The method for producing the present compound by reacting the carboxylic acid compound shown by the formula (II):

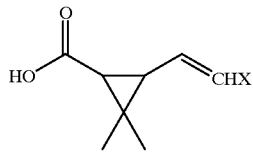

wherein X has the same meaning defined above, or its reactive derivative, with the alcohol compound shown by the formula (III):

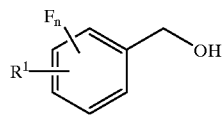

wherein $R^1$ and n have the same meanings defined above, or its reactive derivative.

The reaction is usually carried out in an organic solvent. It may be done in the presence of a condensing agent or while removing by-products from the reaction system if necessary.

The reaction time is usually within a range between 5 minutes and 72 hours and the reaction temperature is usually within a range between –80° C. and the boiling point of the solvent used in the reaction or up to 200° C.

The reactive derivatives of the carboxylic acid compounds shown by the formula (II) are exemplified by acid halides, acid anhydrides, $C_1$–$C_4$ alkyl esters.

The reactive derivatives of the alcohol compounds shown by the formula (III) are exemplified by halides, sulfonate esters, quarternary ammonium salts.

The molar ratio of the carboxylic acid compound shown by the formula (II) or its reactive derivative to the alcohol compound shown by the formula (III) or its reactive derivative can be optionally set and it is preferably equimolecular amount or nearby.

The examples of the condensing agents include organic bases such as tertiary amines (triethylamine, 4-dimethyaminopyridine, diisopropylethylamine and the like), nitrogen-containing aromatic compounds (pyridine and the like), alkali metal alkoxides (sodium methoxide, potassium tert-butoxide and the like); inorganic bases such as sodium hydroxide, potassium carbonate; Lewis acids such as titanium (IV) phenoxide, proton acids (e.g. p-toluenesulfonic acid, sulfuric acid), etc.; dicyclohexylcarbodiimide; 1-ethyl-3-(3-dimethylaminopropyl)carbodiimide hydrochloride; diethyl azodicarboxylatetriphenylphosphine.

These condensing agents are suitably selected according to the kind of the carboxylic acid compounds shown by the formula (II) or its reactive derivatives or the kind of the alcohol compounds shown by the formula (III) or its reactive derivatives. The amount of the reagents are suitably selected according to the type of the reaction.

Examples of the solvent include hydrocarbons such as benzene, toluene, hexane and the like; ethers such as diethyl ether, tetrahydrofuran and the like; halogenated hydrocarbons such as dichloromethane, 1,2-dichloroethane and the like; amides such as dimethylformamide and the like; and ketones such as acetone and the like.

After the completion of the reaction, the reaction solution can be subjected to a usual work-up treatment such as extraction with organic solvent, concentration, and so on to give the present compound. If necessary, it may be purified by usual procedure such as chromatography, distillation, recrystallization and/or the like.

The carboxylic acid compounds shown by the formula (II) or its reactive derivatives can be prepared according to the methods described in J. Chem. Soc. 1076 (1970), JP-sho-47-43333A or JP-sho-49-47531A. The alcohol compounds shown by the formula (III) or its reactive derivatives can be prepared according to the methods described in JP-sho-57-123146A, JP-sho-53-79845A or JP-sho-56-97251A.

(Method B)

The method for producing the present compound by reacting the aldehyde compound shown by the formula (IV):

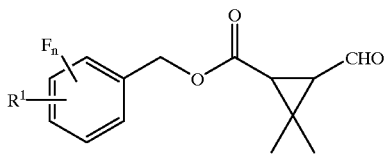

wherein $R^1$ and n have the same meanings defined above, with the phosphorane compound shown by the formula (V):

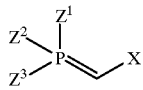

wherein X has the same meaning defined above and $Z^1$, $Z^2$ and $Z^3$ are the same or different and represent $C_1$–$C_8$ alkyl group or optionally substituted phenyl group.

The reaction is usually carried out in a solvent. The reaction time is usually within a range between 5 minutes and 72 hours and the reaction temperature is usually within a range between −80° C. and the boiling point of the solvent used in the reaction or up to 100° C.

Examples of the solvent include hydrocarbons such as benzene, toluene, hexane and the like; ethers such as diethyl ether, tetrahydrofuran and the like; halogenated hydrocarbons such as dichloromethane, 1,2-dichloroethane and the like; amides such as dimethylformamide and the like; and alcohols such as methanol and the like.

The amount of the phosphorane compound shown by the formula (V) used in the reaction is usually from 1 mole to an excess, preferably from 1 mole to 5 moles based on 1 mole of the aldehyde compound shown by the formula (IV).

After the completion of the reaction, the reaction solution can be subjected to a usual work-up treatment such as filtration, extraction with organic solvent, concentration, and so on to give the present compound. If necessary, it may be purified by usual procedure such as chromatography, distillation, recrystallization and/or the like.

The aldehyde compound shown by the formula (IV) can be prepared according to the method described in JP-sho-49-47531A and the phosphorane compound shown by the formula (V) can be prepared according to the method described in "Jikkenkagakukoza" (Experimental Chemistry Course) (4th ed., Maruzen Co.) vol. 19, 59.

The present compounds have optical isomers (R, S) based on an asymmetric carbon, geometrical isomers (E, Z) based on a double bond and geometrical isomers (cis, trans) based on a cyclopropane ring. The present invention includes all the optical isomers, geometrical isomers and their mixtures having pesticidal activity.

Examples of the carboxylic acid compounds shown by the formula (II) include the followings:
2,2-dimethyl-3-vinylcyclopropanecarboxlic acid
2,2-dimethyl-3-(1-propenyl)cyclopropanecarboxlic acid
3-(1-butenyl)-2,2-dimethylcyclopropanecarboxlic acid Examples of the alcohol compounds shown by the formula (III) include the followings:
(2,3,5,6-tetrafluorophenyl)methanol
(2,3,5,6-tetrafluoro-4-methylphenyl)methanol
(2,3,5,6-tetrafluoro-4-methoxyphenyl)methanol
(2,3,4,5,6-pentafluorophenyl)methanol Examples of the aldehyde compounds shown by the formula (IV) include the followings:
(2,3,5,6-tetrafluoro-4-methylphenyl)methyl 3-formyl-2,2-dimethylcyclopropanecarboxylate Examples of the phosphorane compounds shown by the formula (V) include the followings:
1-triphenylphosphoranylideneethane
1-triphenylphosphoranylidenepropane
1-triphenylphosphoranylidenebutane Examples of noxious pests (noxious insects/acarina) against which the present compound exhibits a control effect include the followings:
Hemiptera
Delphacidae (planthoppers) such as *Laodelphax striatellus* (small brown planthopper), *Nilaparvata lugens* (brown planthopper), *Sogatella furcifera* (white backed rice planthopper); leafhoppers such as *Nephotettix cincticeps*, *Nephotettix virescens*; Aphididae (aphids); plant bugs; Aleyrodidae (whiteflies); scales; Tingidae (lace bugs); Psyllidae; and so on;
Lepidoptera
Pyralidae such as *Chilo suppressalis* (rice stem borer), *Cnaphalocrocis medinalis* (rice leafroller), *Plodia interpunctella* (Indian meal moth); Noctuidae such as *Spodoptera litura* (tobacco cutworm), *Pseudaletia separata* (rice armyworm), *Mamestra brassicae* (cabbage armyworm); Pieridae such as *Pieris rapae crucivora* (common cabbageworm), Tortricidae such as *Adoxophyes* spp.; Carposinidae; Lyonetiidae; Lymantriidae; Plusiinae; *Agrotis* spp. such as *Agrotis segetum* (turnip cutworm), *Agrotis epsilon* (black cutworm); *Helicoverpa* spp.; *Heliotis* spp.; *Plutella xylostella* (diamondback moth); *Parnara guttata* (rice skipper); *Tinea pellionella* (casemaking clothes moth); *Tineola bisselliella* (webbing clothes moth); and so on;
Diptera
*Culex* spp. such as *Culex pipiens pallens* (common mosquito), *Culex tritaeniorhynchus*; *Aedes* spp. such as *Aedes aegypti, Aedes albopictus*; *Anopheles* spp. such as *Anopheles sinensis*; Chironomidae (midges); Muscidae such as *Musca domestica* (housefly), *Muscina stabulans* (false stablefly); Calliphoridae; Sarcophagidae; Anthomyiidae such as *Delia platura* (seedcorn maggot), *Fannia canicularis* (little housefly), *Delia antiqua* (onion maggot); Tephritidae (fluit flies); Drosophilidae; Psychodidae (moth flies); Tabanidae; Simuliidae (black flies); Stomoxyidae; and so on;
Coleoptera (beetles)
corn rootworms such as *Diabrotica virgifera* (western corn rootworm), *Diabrotica undecimpunctata howardi* (southern corn rootworm); Scarabaeidae such as *Anomala cuprea* (cupreous chafer), *Anomala rufocuprea* (soybean beatle); weevils such as *Sitophilus zeamais* (maize weevil), *Lissorhoptrus oryzophilus* (ricewater weevil), ball weevil, *Callosobruchus chinensis* (adzuki bean weevil); Tenebrionidae (darkling beetles) such as *Tenebrio molitor* (yellow mealworm), *Tribolium castaneum* (red flour beetle); Chrysomelidae (leaf beetles) such as *Oulema oryzae* (rice leaf beetle), *Phyllotreta striolata* (striped flea beetle), *Aulacophora femoralis* (cucurbit leaf beetle); Anobiidae; *Epilachna* spp. such as *Epilachna vigintioctopunctata* (twenty-eight-spotted ladybird); Lyctidae (powderpost beetles); Bostrychidae (false powderpost beetles); Cerambycidae; *Paederus fuscipes* (robe beetle); and so on;
Dictyoptera
*Blattella germanica* (German cockroach); *Periplaneta fuliginosa* (smokybrown cockroach); *Periplaneta americana* (American cockroach); *Periplaneta brunnea* (brown cockroach); *Blatta orientalis* (oriental cockroach); and so on;
Thysanoptera
*Thrips palmi*; western flower thrips; *Thrips hawaiiensis*; and so on;

Hymenoptera

Formicidae (ants); Vespidae (hornets); Bethylidae; Tenthredinidae (sawflies) such as *Athalis rosae ruficornis* (cabbage sawfly); and so on;

Orthoptera

Gryllotalpidae (mole crickets); Acrididae (grasshoppers); and so on;

Siphonaptera

*Pulex irritans; Ctenocephalides felis* (cat flea); and so on;

Anoplura

*Pediculus humanus humanus* (body louse); *Pthirus pubis* (crab louse); and so on;

Isoptera

*Reticulitermes speratus, Coptotermes formosanus* (Formosan subterranean termite); and so on;

House-dust Mites

Dermanyssidae such as *Dermatophagoides farinae* (American house dust mite), *Dermatophagoides pteronyssinus*; Acaridae such as *Tyrophagus putrescentiae* (mold mite), *Aleuroglyphus ovatus*; and so on;

The Other Mites

Glycyphagidae such as *Glycyphagus privatus, Glycyphagus domesticus, Glycyphagus destructor*; Cheyletidae such as *Chelacaropsis malaccensis, Cheyletus fortis*; Tarsonemidae; *Chortoglyphus* spp.; *Haplochthonius simplex* and the like; Tetranychidae such as *Tetranychus urticae* (carmine spider mite); *Tetranychus kanzawai* (Kanzawa spider mite); *Panonychus citri* (citrus red mite); *Panonychus ulmi* (European red mite); and so on;

Ticks

Ixodidae such as *Haemaphysalis longiconis*;

The present compounds are also effective for controlling the pests resistant against known insecticides/acaricides.

The pesticides in the present invention are for killing or repelling pests.

The present compound to be used as an active ingredient of a pesticide is usually formulated by mixing with a solid carrier, a liquid carrier, a gaseous carrier or bait, or is impregnated with a base material of a mosquito-coil or mosquito-mat for electric heating fumigation. The present compound is used as formulation such as oil solutions, emulsifiable concentrates, wettable powders, flowable formulations (aqueous suspension, aqueous emulsion, etc.), granules, dusts, aerosols, volatile formulations such as mosquito-coil, mosquito-mats for electric heater and liquid for electric heater, heating fumigants such as combustible fumigant, chemical fumigant and a porous ceramic fumigant, non-heating volatile formulations applied on resin or paper, fogging formulations, ULV formulations (formulations for ultra low volume application) and poisonous bait. Surfactants or other auxiliaries are added to the formulation if necessary.

These formulations include the present compound as an active ingredient in an amount of 0.001% to 95% by weight.

Examples of the solid carrier to be used for the formulation include fine powder or granules of clays (e.g. kaolin clay, diatomaceous earth, synthetic hydrated silicon oxide, bentonite, Fubasami clay, acid clay), talc, ceramics, other inorganic minerals (e.g. sericite, quartz, sulfur, active carbon, calcium carbonate, hydrated silicon oxide), chemical fertilizer (e.g. ammonium sulfate, ammonium phosphate, ammonium nitrate, urea, ammonium chloride) and the like. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosine, gas oil), esters (ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (dichloromethane, trichloroethane, carbon tetrachloride), dimethyl sulfoxide, vegetable oils (e.g. soybean oil, cottonseed oil). Examples of the gaseous carrier or propellant to be used for the formulation include flon gas, butane gas, LPG (liquefied petroleum gas), dimethyl ether and carbon dioxide.

Examples of the surfactant include alkyl sulfate salts, alkylsulfonate salts, alkylarylsulfonate salts, alkyl aryl ethers, polyoxyethylenealkyl aryl ethers, polyethylene glycol ethers, polyhydric alcohol esters and sugar alcohol derivatives.

Examples of the sticking agents, the dispersing agent, and other auxiliaries include casein, gelatin, polysaccharides (e.g. starch, gum arabic, cellulose derivatives, alginic acid), lignin derivatives, bentonite, sugars and synthetic water-soluble polymers (e.g. polyvinyl alcohol, polyvinylpyrrolidone, polyacrylic acids). Examples of the stabilizer include PAP (acid isopropyl phosphate), BHT (2,6-di-tert-butyl-4-methyphenol), BHA (mixture of 2-tert-butyl-4-methoxyphenol and 3-tert-butyl-4-methoxyphenol), vegetable oils, mineral oils, surfactants, fatty acids and esters of fatty acid.

The base materials of the poisonous baits include a bait component (e.g. grain powder, vegetable oil, sugar, crystalline cellulose), an antioxidant (e.g. dibutylhydroxytoluene, nordihydroguaiaretic acid), a preservative (e.g. dehydroacetic acid), a substance for preventing erroneous eating (e.g. red pepper powder), an attractant (e.g. cheese flavor, onion flavor, peanut oil) and the like.

The flowable formulations (aqueous suspension or aqueous emulsion) are usually prepared by finely dispersing the present compound at a ratio of 1 to 75% in water containing a 0.5 to 15% dispersing agent, a 0.1 to 10% suspension assistant (for example, protective colloid or a compound giving thixotropy) and 0 to 10% additives (e.g. an antifoamer, a rust preventive agent, a stabilizer, a developing agent, a penetrating assistant, antifreezing agent, a bactericide, a fungicide). The present compound may be dispersed in oil, in which the present compound is substantially insoluble, to form oil suspensions.

Examples of the protective colloid include gelatin, casein, gums, cellulose ethers and polyvinyl alcohol. Examples of the compound giving thixotropy include bentonite, aluminum magnesium silicate, xanthan gum and polyacrylic acid.

The formulations thus obtained is used as prepared or diluted with water and may be used simultaneously with another insecticide, acaricide, nematocide, soil disinfectant, fungicide, herbicide, plant growth regulator, synergist, fertilizer, soil-improving agent and/or repellent under non-mixed conditions or pre-mixed conditions.

Examples of the insecticide, nematocide, acaricide and soil disinfectant include organophosphorus compounds such as fenitrothion [O,O-dimethyl O-(3-methyl-4-nitrophenyl) phosphorothioate], fenthion [O,O-dimethyl O-(3-methyl-4-(methythio)phenyl)phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [O,S-dimethyl acetylphosphoramidothioate], methidathion[S-2,3-dihydro-5-methoxy-2-oxo-1,3,4-thiadiazol-3-ylmethyl O,O-dimethyl phosphorodithioate], disulfoton [O,O-diethyl S-2-ethylthioethyl phosphorodithioate], DDVP [2,2-dichlorovinyl dimethyl phosphate], sulprofos [O-ethyl O-4-

(methylthio)phenyl S-propyl phosphorodithioate], cyanophos [O-4-cyanophenyl O,O-dimethyl phosphorothioate], dioxabenzofos [2-methoxy-4H-1,3,2-benzodioxaphosphorin-2-sulfide], dimethoate [O,O-dimethyl S-(N-methylcarbamoylmethyl)dithiophosphate], phenthoate [ethyl 2-dimethoxyphosphinothioylthio(phenyl) acetate], malathion [diethyl(dimethoxyphosphinothioylthio) succinate], trichlorfon [dimethyl 2,2,2-trichloro-1-hydroxyethylphosphonate], azinphos-methyl [S-3,4-dihydro-4-oxo-1,2,3-benzotriazin-3-ylmethyl O,O-dimethyl phosphorodithioate], monocrotophos [dimethyl{(E)-1-methyl-2-(methylcarbamoyl)vinyl}phosphate] and ethion [O,O,O',O'-tetraethyl S,S'-methylene bis(phosphorodithioate)], carbamate compounds such as BPMC [2-sec-butylphenyl methylcarbamate], benfracarb [ethyl N-{2,3-dihydro-2,2-dimethylbenzofuran-7-yloxycarbonyl(methyl)aminothio}-N-isopropyl-β-alaninate], propoxur [2-isopropoxyphenyl N-methylcarbamate], carbosulfan [2,3-dihydro-2,2-dimethyl-7-benzo[b]furanyl N-dibuthylaminothio-N-methylcarbamate], carbaryl [1-naphthyl N-methylcarbamate], methomyl [S-methyl-N-(methylcarbamoyloxy)thioacetimidate], ethiofencarb [2-(ethylthiomethyl)phenyl methylcarbamate], aldicarb [2-methyl-2-(methylthio)propionaldehyde O-methylcarbamoyloxime], oxamyl [N,N-dimethyl-2-methylcarbamoyloxyimino-2-(methylthio)acetamide] and fenothiocarb [S-4-phenoxybuthyl-N,N-dimethyl-thiocarbamate], pyrethroid compounds such as etofenprox [2-(4-ethoxyphenyl)-2-methyl-1-(3-phenoxybenzyl) oxypropane], fenvalerate [(RS)-α-cyano-3-phenoxybenzyl (RS)-2-(4-chlorophenyl)-3-methylbutyrate], esfenvalerate [(S)-α-cyano-3-phenoxybenzyl(S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS)-cis,trans-3-(2,2-dichlorovinyl)-2,2-dimethylcyclopropanecarboxylate], permethrin [3-phenoxybenzyl(1RS)-cis,trans-3-(2,2-dichlorovinyl)-2,2-dimethylcyclopropanecarboxylate], cyhalothrin [(RS)-α-cyano-3-phenoxybenzyl(1RS,3Z)-cis-3-(2-chloro-3,3,3-trifluoroprop-1-enyl)-2,2-dimethylcyclopropanecarboxylate], deltamethrin [(S)-α-cyano-3-phenoxybenzyl(1R)-cis-3-(2,2-dibromovinyl)-2,2-dimethylcyclopropanecarboxylate], cycloprothrin [(RS)-α-cyano-3-phenoxybenzyl(RS)-2,2-dichloro-1-(4-ethoxyphenyl)cyclopropanecarboxylate], fluvalinate [α-cyano-3-phenoxybenzyl N-(2-chloro-α,α,α-trifluoro-p-tolyl)-D-valinate], bifenthrin [2-methyl-3-phenylbenzyl(1RS,3Z)-cis-3-(2-chloro-3,3,3-trifluoro-1-propenyl)-2,2-dimethylcyclopropanecarboxylate], halfenprox [2-(4-bromodifluoromethoxyphenyl)-2-methyl-1-(3-phenoxybenzyl)methylpropane], tralomethrin [(S)-α-cyano-3-phenoxybenzyl(1R)-cis-3-(1,2,2,2-tetrabromoethyl)-2,2-dimethylcyclopropanecarboxylate], silafluofen [(4-ethoxyphenyl)-{3-(4-fluoro-3-phenoxyphenyl)propyl}dimethylsilane], d-phenothrin [3-phenoxybenzyl(1R)-cis,trans-2,2-dimethyl-3-(2-methyl-1-propenyl)cyclopropanecarboxylate], cyphenothrin [(RS)-α-cyano-3-phenoxybenzyl(1R)-cis,trans-2,2-dimethyl-3-(2-methyl-1-propenyl)cyclopropanecarboxylate], d-resmethrin [5-benzyl-3-furylmethyl(1R)-cis,trans-2,2-dimethyl-3-(2-methyl-1-propenyl)cyclopropanecarboxylate], acrinathrin [(S)-α-cyano-3-phenoxybenzyl(1R,3Z)-cis-2,2-dimethyl-3-{3-oxo-3-(1,1,1,3,3,3-hexafluoropropyloxy) propenyl}cyclopropanecarboxylate], cyfluthrin [(RS)-α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl(1RS,3Z)-cis-3-(2-chloro-3,3,3-trifluoro-1-propenyl)-2,2-dimethylcyclopropanecarboxylate], transfluthrin [2,3,5,6-tetrafluorobenzyl(1R)-trans-3-(2,2-dichlorovinyl)-2,2-dimethylcyclopropanecarboxylate], tetramethrin [3,4,5,6-tetrahydrophthalimidomethyl(1RS)-cis,trans-2,2-dimethyl-3-(2-methyl-1-propenyl) cyclopropanecarboxylate], allethrin [(RS)-2-methyl-4-oxo-3-(2-propenyl)-2-cyclopenten-1-yl(1RS)-cis,trans-2,2-dimethyl-3-(2-methyl-1-propenyl)cyclopropanecarboxylate], prallethrin [(S)-2-methyl-4-oxo-3-(2-propynyl)-2-cyclopenten-1-yl(1R)-cis,trans-2,2-dimethyl-3-(2-methyl-1-propenyl)cyclopropanecarboxylate], empenthrin [(RS)-1-ethynyl-2-methyl-2-pentenyl(1R)-cis,trans-2,2-dimethyl-3-(2-methyl-1-propenyl)cyclopropanecarboxylate], imiprothrin [2,5-dioxo-3-(2-propynyl)imidazolidin-1-ylmethyl(1R)-cis,trans-2,2-dimethyl-3-(2-methyl-1-propenyl)cyclopropanecarboxylate], d-furamethrin [5-(2-propynyl)furfuryl(1R)-cis,trans-2,2-dimethyl-3-(2-methyl-1-propenyl)cyclopropanecarboxylate] and 5-(2-propynyl) furfuryl 2,2,3,3-tetramethylcyclopropanecarboxylate, thiadiazine derivatives such as buprofezin [2-tert-butylimino-3-isopropyl-5-phenyl-1,3,5-thiadiazin-4-one], nitroimidazolidine derivatives, nereistoxin derivatives such as cartap [S,S'-(2-dimethylaminotrimethylene)bis (thiocarbamate)], thiocyclam [N,N-dimethyl-1,2,3-trithian-5-ylamine], bensultap [S,S'-2-dimethylaminotrimethylenedi (benzenesulfonate)], N-cyanoamidine derivatives such as N-cyano-N'-methyl-N''-(6-chloro-3-pyridylmethyl) acetamidine, chlorinated hydrocarbons such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane] and dicofol [1,1-bis (4-chlorophenyl)-2,2,2-trichloroethanol], benzoylphenylurea compounds such as chlorfluazuron [1-{3,5-dichloro-4-(3-chloro-5-trifluoromethylpyridyn-2-yloxy)phenyl}-3-(2,6-difluorobenzoyl)urea], teflubenzuron [1-(3,5-dichloro-2,4-difluorophenyl)-3-(2,6-difluorobenzoyl)urea] and flufenoxuron [1-{4-(2-chloro-4-trifluoromethylphenoxy)-2-fluorophenyl}-3-(2,6-difluorobenzoyl)urea], formamidine derivatives such as amitraz [N,N'-{(methylimino) dimethylidine}-di-2,4-xylidine] and chlordimeform [N'-(4-chloro-2-methylphenyl)-N,N-dimethylmethanimidamide], thiourea derivatives such as diafenthiuron [N-(2,6-diisopropyl-4-phenoxyphenyl)-N'-t-butylcarbodiimide], N-phenylpyrazole compounds, metoxadiazone [5-methoxy-3-(2-methoxyphenyl)-1,3,4-oxadiazol-2-(3H)-one], bromopropylate [isopropyl 4,4'-dibromobenzilate], tetradifon [4-chlorophenyl 2,4,5-trichlorophenyl sulfone], chinomethionat [S,S-6-methylquinoxaline-2,3-diyldithiocarbonate], propargite [2-(4-tert-butylphenoxy)cyclohexylprop-2-yl sulfite], fenbutatin oxide [bis{tris (2-methyl-2-phenylpropyl)tin}oxide], hexythiazox [(4RS,5RS)-5-(4-chlorophenyl)-N-chlorohexyl-4-methyl-2-oxo-1,3-thiazolidine-3-carboxamide], clofentezine [3,6-bis(2-chlorophenyl)-1,2,4,5-tetrazine], pyridaben [2-tert-butyl-5-(4-tert-butylbenzylthio)-4-chloropyridazin-3(2H)-one], fenpyroximate [tert-butyl (E)-4-[{(1,3-dimethyl-5-phenoxypyrazol-4-yl)methyleneaminooxymethyl} benzoate], tebufenpyrad [N-(4-tert-butylbenzyl)-4-chloro-3-ethyl-1-methyl-5-pyrazolecarboxamide], polynactins complex [tetranactin, dinactin and trinactin], pyrimidifen [5-chloro-N-[2-{4-(2-ethoxyethyl)-2,3-dimethyl-phenoxy}ethyl]-6-ethylpyrimidin-4-amine], milbemectin, abamectin, ivermectin and azadirachtin [AZAD].

Examples of the repellents include 3,4-caranediol, N,N-diethyl-m-toluamide, 1-methylpropyl 2-(2-hydroxyethyl)-1- piperidinecarboxylate, p-menthan-3,8-diol, plant essential oil such as hyssop oil and the like.

Examples of the synergists include bis(2,3,3,3-tetrachloropropyl)ether (S-421), N-(2-ethylhexyl)bicyclo[2.2.1]hept-5-ene-2,3-dicarboximide (MGK-264) and α-[2-(2-butoxyethoxy)ethoxy]-4,5-methylenedioxy-2-propyltoluene (piperonylbutoxide).

When the present compound is applied as an active ingredient of pesticides for agricultural use, the dosage is usually from 5 to 500 g per 10 are. When emulsifiable concentrates, wettable powders or flowable formulations is diluted with water and applied, the concentration is usually from 0.1 to 10000 ppm. Granuls, dusts, resin formulations and so on are used as prepared.

When the present compound is applied as an active ingredient of pesticides for house-hold use or animal-health use, emulsifiable concentrates, wettable powders and flowable formulations are usually diluted with water to the concentration of 0.1 to 10000 ppm. Oil solutions, aerosols, fumigants, fogging agents, smokings, volatile agents, ULV formulations, poisonous baits and resin formulations and so on are used as prepared.

The amount and concentration of application may be varied optionally according to the type of the formulations; time, place, and method of application; kind of noxious pests and damage and may be increased or decreased in spite of the above-mentioned range.

EXAMPLES

The present invention will be further illustrated in detail by the production examples, formulation examples and biological tests, although the present invention is not limited in any sense to these examples.

The production examples are shown as follows. The number of the present compounds is described in Table 1 below.

Production Example 1

To a mixture solution of 1.78 g of (2,3,5,6-tetrafluoro-4-methylphenyl)methanol, 0.87 g of pyridine and 20 ml of tetrahydrofuran, 2.06 g of (1R)-trans-2,2-dimethyl-3-(2-methyl-1-propenyl)cyclopropanecarboxylic chloride was added under ice-cooling and the mixture was stirred for 8 hours at room temperature. The reaction mixture was poured into about 100 ml of ice-water and extracted with each 100 ml of ethyl acetate twice. The combined ethyl acetate was washed with saturated brine, dried over anhydrous sodium sulfate and concentrated under reduced pressure to give a crude product, which was subjected to silica gel column chromatography (eluent: hexane/ethyl acetate=20/1) to give 2.75 g of (2,3,5,6-tetrafluoro-4-methylphenyl)methyl(1R)-trans-2,2-dimethyl-3-(2-methyl-1-propenyl)cyclopropanecarboxylate (yield 87%).

Into a mixture solution of 1.27 g of (2,3,5,6-tetrafluoro-4-methylphenyl)methyl(1R)-trans-2,2-dimethyl-3-(2-methyl-1-propenyl)cyclopropanecarboxylate, 20 ml of methanol and 20 ml of ethyl acetate, oxygen containing ozone was blown at −78° C. until the color of the solution was changed to blue. Then nitrogen gas was blown into the solution for removing excess ozone, 5 ml of dimethylsulfide was added to the solution and the solution was brought to room temperature. After one day, the reaction solution was concentrated under reduced pressure. To the residue, 20 ml of acetone, 2 ml of water and 0.2 g of p-toluenesulfonic acid monohydrate were added and allowed to stand at room temperature for 2 hours. The reaction solution was poured into water and extracted with diethyl ether. The organic layer was dried over anhydrous sodium sulfate and concentrated under reduced pressure to give a residue, which was subjected to silica gel column chromatography (eluent: hexane/ethyl acetate=10/1) to give 0.98 g of (2,3,5,6-tetrafluoro-4-methylphenyl)methyl(1R)-trans-3-formyl-2,2-dimethylcyclopropanecarboxylate (yield 82%). m.p. 43.2° C.

A mixture of 1.1 g of ethyltriphenylphosphonium bromide and 30 ml of terahydrofuran was cooled by ice and 0.23 g of potassium tert-butoxide was added to the mixture under stirring. After 15 minutes, a tetrahydrofuran (5 ml) solution containing 0.32 g of (2,3,5,6-tetrafluoro-4-methylphenyl)methyl (1R)-trans-3-formyl-2,2-dimethylcyclopropanecarboxylate was added to the mixture. After 30 minutes, the reaction mixture was filtered with celite and the filtrate was concentrated under reduced pressure. The residue was subjected to silica gel column chromatography (eluent: hexane/ethyl acetate=20/1) to give 0.22 g of (2,3,5,6-tetrafluoro-4-methylphenyl)methyl(1R)-trans-2,2-dimethyl-3-((Z)-1-propenyl)cyclopropanecarboxylate (Present compound 1) (yield 67%).

$^1$H-NMR (CDCl$_3$, TMS) δ 1.14(3H,s), 1.28(3H,s), 1.45 (1H,d,J=5.3), 1.70(3H,dd,J=7.0,1.7), 2.17(1H,brdd,J=8.4, 5.3), 2.28(2H,t, J=2.1),5.11(1H,ddq,J=10.7,8.4,1.7),5.20 (1H,t,J=1.5),5.21(1H, t,J=1.5), 5.59(1H,dqd, J=10.7,7.0,1.3)

Production Example 2

To a mixture solution of 0.42 g of (1R)-trans-2,2-dimethyl-3-((Z)-1-propenyl)cyclopropanecarboxylic acid, 0.49 g of (2,3,5,6-tetrafluorophenyl)methanol, 0.93 g of triphenylphosphine and 20 ml of tetrahydrofuran, 2.0 ml of 40% toluene solution containing diisopropyl azodicarboxylate was added. After one day, the reaction solution was concentrated under reduced pressure and the residue was subjected to silica gel column chromatography (eluent: hexane/ethyl acetate=20/1) to give 0.80 g of (2,3,5,6-tetrafluorophenyl)methyl (1R)-trans-2,2-dimethyl-3-((Z)-1-propenyl)cyclopropanecarboxylate (Present compound 2) (yield 93%).

$^1$H-NMR (CDCl$_3$, TMS) δ 1.15(3H,s), 1.29(3H,s), 1.47 (1H,d,J=5.3), 1.70(3H,dd,J=6.9,1.6), 2.19(1H,brdd,J=8.1, 5.3), 5.12(1H,d, J=10.6, 8.1,1.6), 5.24(1H,t, J=1.6), 5.25 (1H,t,J=1.6), 5.60(1H,dqd,J=10.6,6.9,1.1), 7.10 (1H,tt,J=9.7, 7.4)

Production Example 3

To a mixture solution of 0.50 g of (1RS)-trans-2,2-dimethyl-3-((E)-1-propenyl)cyclopropanecarboxylic acid, 0.72 g of 1-bromomethyl-2,3,5,6-tetrafluoro-4-methylbenzene and 8 ml of dimethylformamide, 1.0 g of triethylamine was added and the mixture was stirred at 80° C. for 4 hours. After the mixture was cooled to room temperature, water was poured into the mixture and the mixture was extracted with diethyl ether. The organic layer was dried over anhydrous magnesium sulfate and concentrated under reduced pressure. The residue was subjected to silica gel column chromatography (eluent: hexane/ethyl acetate=20/1) to give 0.83 g of (2,3,5,6-tetrafluoro-4-methylphenyl)methyl(1RS)-trans-2,2-dimethyl-3-((E)-1-propenyl)cyclopropanecarboxylate (Present compound 3) (yield 90%).

$^1$H-NMR (CDCl$_3$, TMS) δ 1.13(3H,s), 1.24(3H,s), 1.47 (1H,d,J=5.4), 1.68(3H,dd,J=6.5,1.5), 2.02(1H,dd,J=8.2,5.4), 2.28(3H,t,J=2.0), 5.15–5.23(3H,m), 5.61(1H,dq,J=14.9,6.5)

Table 1 shows the examples of the present compounds shown by the formula (I) with compound numbers. In table 1, the positions of $R^1$ and $F_n$ are shown when acyloxymethyl group is set at 1-position and E/Z in the isomerism of acid component shows metric isomerism based on the double bond bonded with X group.

TABLE 1

| Compound Nos. | $R^1$ | Position substituted by $F_n$ | X | Isomerism of acid component |
|---|---|---|---|---|
| 1 | 4-Me | 2,3,5,6 | Me | 1R-trans-Z |
| 2 | 4-H | 2,3,5,6 | Me | 1R-trans-Z |
| 3 | 4-Me | 2,3,5,6 | Me | 1RS-trans-E |
| 4 | 4-F | 2,3,5,6 | Me | 1R-trans-Z |
| 5 | 4-allyl | 2,3,5,6 | Me | 1RS-trans-E |
| 6 | 4-MeO | 2,3,5,6 | Me | 1R-trans-Z |
| 7 | 4-Me | 2,3,5,6 | Et | 1R-trans-Z |
| 8 | 4-Me | 2,3,5,6 | H | 1R-trans |
| 9 | 4-Me | 2,3,5,6 | H | 1R-cis |
| 10 | 2-Cl | 6 | Me | 1R-cis |
| 11 | 4-H | 2,3,5,6 | H | 1R-trans |
| 12 | 4-F | 2,3,5,6 | H | 1R-trans |
| 13 | 4-Me | 2,3,5,6 | H | 1R-trans |
| 14 | 4-vinyl | 2,3,5,6 | H | 1R-trans |
| 15 | 4-allyl | 2,3,5,6 | H | 1R-trans |
| 16 | 4-$CF_3$ | 2,3,5,6 | H | 1R-trans |
| 17 | 4-$MeOCH_2$ | 2,3,5,6 | H | 1R-trans |
| 18 | 4-MeO | 2,3,5,6 | H | 1R-trans |
| 19 | 4-MeS | 2,3,5,6 | H | 1R-trans |
| 20 | 2-H | 3,4,5,6 | H | 1R-trans |
| 21 | 2-Me | 3,4,5,6 | H | 1R-trans |
| 22 | 3-$CF_3O$ | 2,4,5,6 | H | 1R-trans |
| 23 | 2-Cl | 6 | H | 1R-trans |
| 24 | 2-$CF_3$ | 6 | H | 1R-trans |
| 25 | 3-H | 2,4 | H | 1R-trans |
| 26 | 3-H | 2,6 | H | 1R-trans |
| 27 | 3-H | 2,4,6 | H | 1R-trans |
| 28 | 3-Br | 4 | H | 1R-trans |
| 29 | 3-$CHF_2$ | 2,4,6 | H | 1R-trans |
| 30 | 4-allyl | 2,6 | H | 1R-trans |
| 31 | 4-allyl | 3,5 | H | 1R-trans |
| 32 | 4-H | 2,3,5,6 | H | 1R-cis |
| 33 | 4-F | 2,3,5,6 | H | 1R-cis |
| 34 | 4-Me | 2,6 | H | 1R-cis |
| 35 | 4-vinyl | 2,3,5,6 | H | 1R-cis |
| 36 | 4-allyl | 2,3,5,6 | H | 1R-cis |
| 37 | 4-$CF_3$ | 2,3,5,6 | H | 1R-cis |
| 38 | 4-$MeOCH_2$ | 2,3,5,6 | H | 1R-cis |
| 39 | 4-MeO | 2,3,5,6 | H | 1R-cis |
| 40 | 4-MeS | 2,3,5,6 | H | 1R-cis |
| 41 | 2-H | 3,4,5,6 | H | 1R-cis |
| 42 | 2-Me | 3,4,5,6 | H | 1R-cis |
| 43 | 3-$CF_3O$ | 2,4,5,6 | H | 1R-cis |
| 44 | 2-Cl | 6 | H | 1R-cis |
| 45 | 2-$CF_3$ | 6 | H | 1R-cis |
| 46 | 3-H | 2,4 | H | 1R-cis |
| 47 | 3-H | 2,6 | H | 1R-cis |
| 48 | 3-H | 2,4,6 | H | 1R-cis |
| 49 | 3-Br | 4 | H | 1R-cis |
| 50 | 3-$CHF_2$ | 2,4,6 | H | 1R-cis |
| 51 | 4-allyl | 2,6 | H | 1R-cis |
| 52 | 4-allyl | 3,5 | H | 1R-cis |
| 53 | 4-Et | 2,3,5,6 | Me | 1R-trans-Z |
| 54 | 4-F | 2,6 | Me | 1R-trans-Z |
| 55 | 4-Me | 2,6 | Me | 1R-trans-Z |
| 56 | 4-vinyl | 2,3,5,6 | Me | 1R-trans-Z |
| 57 | 4-allyl | 2,3,5,6 | Me | 1R-trans-Z |
| 58 | 4-$CF_3$ | 2,3,5,6 | Me | 1R-trans-Z |
| 59 | 4-$MeOCH_2$ | 2,3,5,6 | Me | 1R-trans-Z |
| 60 | 4-MeO | 2,6 | Me | 1R-trans-Z |
| 61 | 4-MeS | 2,3,5,6 | Me | 1R-trans-Z |
| 62 | 2-H | 3,4,5,6 | Me | 1R-trans-Z |
| 63 | 2-Me | 3,4,5,6 | Me | 1R-trans-Z |
| 64 | 3-$CF_3O$ | 2,4,5,6 | Me | 1R-trans-Z |
| 65 | 2-Cl | 6 | Me | 1R-trans-Z |
| 66 | 2-$CF_3$ | 6 | Me | 1R-trans-Z |
| 67 | 3-H | 2,4 | Me | 1R-trans-Z |
| 68 | 3-H | 2,6 | Me | 1R-trans-Z |
| 69 | 3-H | 2,4,6 | Me | 1R-trans-Z |
| 70 | 3-Br | 4 | Me | 1R-trans-Z |
| 71 | 3-$CHF_2$ | 2,4,6 | Me | 1R-trans-Z |
| 72 | 4-allyl | 2,6 | Me | 1R-trans-Z |
| 73 | 4-allyl | 3,5 | Me | 1R-trans-Z |
| 74 | 4-H | 2,3,5,6 | Me | 1R-trans-E |
| 75 | 4-F | 2,3,5,6 | Me | 1R-trans-E |
| 76 | 4-Me | 2,3,5,6 | Me | 1R-trans-E |
| 77 | 4-vinyl | 2,3,5,6 | Me | 1R-trans-E |
| 78 | 4-allyl | 2,3,5,6 | Me | 1R-trans-E |
| 79 | 4-$CF_3$ | 2,3,5,6 | Me | 1R-trans-E |
| 80 | 4-$MeOCH_2$ | 2,3,5,6 | Me | 1R-trans-E |
| 81 | 4-MeO | 2,3,5,6 | Me | 1R-trans-E |
| 82 | 4-MeS | 2,3,5,6 | Me | 1R-trans-E |
| 83 | 2-H | 3,4,5,6 | Me | 1R-trans-E |
| 84 | 2-Me | 3,4,5,6 | Me | 1R-trans-E |
| 85 | 3-$CF_3O$ | 2,4,5,6 | Me | 1R-trans-E |
| 86 | 2-Cl | 6 | Me | 1R-trans-E |
| 87 | 2-$CF_3$ | 6 | Me | 1R-trans-E |
| 88 | 3-H | 2,4 | Me | 1R-trans-E |
| 89 | 3-H | 2,6 | Me | 1R-trans-E |
| 90 | 3-H | 2,4,6 | Me | 1R-trans-E |
| 91 | 3-Br | 4 | Me | 1R-trans-E |
| 92 | 3-$CHF_2$ | 2,4,6 | Me | 1R-trans-E |
| 93 | 4-allyl | 2,6 | Me | 1R-trans-E |
| 94 | 4-allyl | 3,5 | Me | 1R-trans-E |
| 95 | 4-H | 2,3,5,6 | Me | 1R-cis-Z |
| 96 | 4-F | 2,3,5,6 | Me | 1R-cis-Z |
| 97 | 4-Me | 2,3,5,6 | Me | 1R-cis-Z |
| 98 | 4-vinyl | 2,3,5,6 | Me | 1R-Cis-Z |
| 99 | 4-allyl | 2,3,5,6 | Me | 1R-cis-Z |
| 100 | 4-$CF_3$ | 2,3,5,6 | Me | 1R-cis-Z |
| 101 | 4-$MeOCH_2$ | 2,3,5,6 | Me | 1R-cis-Z |
| 102 | 4-MeO | 2,3,5,6 | Me | 1R-cis-Z |
| 103 | 4-MeS | 2,3,5,6 | Me | 1R-cis-Z |
| 104 | 2-H | 3,4,5,6 | Me | 1R-cis-Z |
| 105 | 2-Me | 3,4,5,6 | Me | 1R-cis-Z |
| 106 | 3-$CF_3O$ | 2,4,5,6 | Me | 1R-cis-Z |
| 107 | 2-Cl | 6 | Me | 1R-cis-Z |
| 108 | 2-$CF_3$ | 6 | Me | 1R-cis-Z |
| 109 | 3-H | 2,4 | Me | 1R-cis-Z |
| 110 | 3-H | 2,6 | Me | 1R-cis-Z |
| 111 | 3-H | 2,4,6 | Me | 1R-Cis-Z |
| 112 | 3-Br | 4 | Me | 1R-cis-Z |
| 113 | 3-$CHF_2$ | 2,4,6 | Me | 1R-cis-Z |
| 114 | 4-allyl | 2,6 | Me | 1R-Cis-Z |
| 115 | 4-allyl | 3,5 | Me | 1R-cis-Z |
| 116 | 4-H | 2,3,5,6 | Et | 1R-trans-Z |
| 117 | 4-F | 2,3,5,6 | Et | 1R-trans-Z |
| 118 | 4-Me | 2,6 | Et | 1R-trans-Z |
| 119 | 4-vinyl | 2,3,5,6 | Et | 1R-trans-Z |
| 120 | 4-allyl | 2,3,5,6 | Et | 1R-trans-Z |
| 121 | 4-$CF_3$ | 2,3,5,6 | Et | 1R-trans-Z |
| 122 | 4-$MeOCH_2$ | 2,3,5,6 | Et | 1R-trans-Z |
| 123 | 4-MeO | 2,3,5,6 | Et | 1R-trans-Z |
| 124 | 4-MeS | 2,3,5,6 | Et | 1R-trans-Z |
| 125 | 2-H | 3,4,5,6 | Et | 1R-trans-Z |
| 126 | 2-Me | 3,4,5,6 | Et | 1R-trans-Z |
| 127 | 3-$CF_3O$ | 2,4,5,6 | Et | 1R-trans-Z |
| 128 | 2-Cl | 6 | Et | 1R-trans-Z |
| 129 | 2-$CF_3$ | 6 | Et | 1R-trans-Z |
| 130 | 3-H | 2,4 | Et | 1R-trans-Z |
| 131 | 3-H | 2,6 | Et | 1R-trans-Z |
| 132 | 3-H | 2,4,6 | Et | 1R-trans-Z |
| 133 | 3-Br | 4 | Et | 1R-trans-Z |
| 134 | 3-$CHF_2$ | 2,4,6 | Et | 1R-trans-Z |
| 135 | 4-allyl | 2,6 | Et | 1R-trans-Z |
| 136 | 4-allyl | 3,5 | Et | 1R-trans-Z |
| 137 | 4-H | 2,3,5,6 | Et | 1R-trans-E |
| 138 | 4-F | 2,3,5,6 | Et | 1R-trans-E |
| 139 | 4-Me | 2,3,5,6 | Et | 1R-trans-E |
| 140 | 4-vinyl | 2,3,5,6 | Et | 1R-trans-E |
| 141 | 4-allyl | 2,3,5,6 | Et | 1R-trans-E |
| 142 | 4-$CF_3$ | 2,3,5,6 | Et | 1R-trans-E |
| 143 | 4-$MeOCH_2$ | 2,3,5,6 | Et | 1R-trans-E |
| 144 | 4-MeO | 2,3,5,6 | Et | 1R-trans-E |

TABLE 1-continued

| Compound Nos. | R¹ | Position substituted by $F_n$ | X | Isomerism of acid component |
|---|---|---|---|---|
| 145 | 4-MeS | 2,3,5,6 | Et | 1R-trans-E |
| 146 | 2-H | 3,4,5,6 | Et | 1R-trans-E |
| 147 | 2-Me | 3,4,5,6 | Et | 1R-trans-E |
| 148 | 3-CF$_3$O | 2,4,5,6 | Et | 1R-trans-E |
| 149 | 2-Cl | 6 | Et | 1R-trans-E |
| 150 | 2-CF$_3$ | 6 | Et | 1R-trans-E |
| 151 | 3-H | 2,4 | Et | 1R-trans-E |
| 152 | 3-H | 2,6 | Et | 1R-trans-E |
| 153 | 3-H | 2,4,6 | Et | 1R-trans-E |
| 154 | 3-Br | 4 | Et | 1R-trans-E |
| 155 | 3-CHF$_2$ | 2,4,6 | Et | 1R-trans-E |
| 156 | 4-allyl | 2,6 | Et | 1R-trans-E |
| 157 | 4-allyl | 3,5 | Et | 1R-trans-E |
| 158 | 4-H | 2,3,5,6 | Et | 1R-cis-Z |
| 159 | 4-F | 2,3,5,6 | Et | 1R-cis-Z |
| 160 | 4-Me | 2,3,5,6 | Et | 1R-cis-Z |
| 161 | 4-vinyl | 2,3,5,6 | Et | 1R-cis-Z |
| 162 | 4-allyl | 2,3,5,6 | Et | 1R-cis-Z |
| 163 | 4-CF$_3$ | 2,3,5,6 | Et | 1R-cis-Z |
| 164 | 4-MeOCH$_2$ | 2,3,5,6 | Et | 1R-cis-Z |
| 165 | 4-MeO | 2,3,5,6 | Et | 1R-cis-Z |
| 166 | 4-MeS | 2,3,5,6 | Et | 1R-cis-Z |
| 167 | 2-H | 3,4,5,6 | Et | 1R-cis-Z |
| 168 | 2-Me | 3,4,5,6 | Et | 1R-cis-Z |
| 169 | 3-CF$_3$O | 2,4,5,6 | Et | 1R-cis-Z |
| 170 | 2-Cl | 6 | Et | 1R-cis-Z |
| 171 | 2-CF$_3$ | 6 | Et | 1R-cis-Z |
| 172 | 3-H | 2,4 | Et | 1R-cis-Z |
| 173 | 3-H | 2,6 | Et | 1R-cis-Z |
| 174 | 3-H | 2,4,6 | Et | 1R-cis-Z |
| 175 | 3-Br | 4 | Et | 1R-cis-Z |
| 176 | 3-CHF$_2$ | 2,4,6 | Et | 1R-cis-Z |
| 177 | 4-allyl | 2,6 | Et | 1R-cis-Z |
| 178 | 4-allyl | 3,5 | Et | 1R-cis-Z |
| 179 | 4-H | 2,3,5,6 | Pr | 1R-trans-Z |
| 180 | 4-F | 2,3,5,6 | Pr | 1R-trans-Z |
| 181 | 4-Me | 2,3,5,6 | Pr | 1R-trans-Z |
| 182 | 4-vinyl | 2,3,5,6 | Pr | 1R-trans-Z |
| 183 | 4-allyl | 2,3,5,6 | Pr | 1R-trans-Z |
| 184 | 4-CF$_3$ | 2,3,5,6 | Pr | 1R-trans-Z |
| 185 | 4-MeOCH$_2$ | 2,3,5,6 | Pr | 1R-trans-Z |
| 186 | 4-MeO | 2,3,5,6 | Pr | 1R-trans-Z |
| 187 | 4-MeS | 2,3,5,6 | Pr | 1R-trans-Z |
| 188 | 2-H | 3,4,5,6 | Pr | 1R-trans-Z |
| 189 | 2-Me | 3,4,5,6 | Pr | 1R-trans-Z |
| 190 | 3-CF$_3$O | 2,4,5,6 | Pr | 1R-trans-Z |
| 191 | 2-Cl | 6 | Pr | 1R-trans-Z |
| 192 | 2-CF$_3$ | 6 | Pr | 1R-trans-Z |
| 193 | 3-H | 2,4 | Pr | 1R-trans-Z |
| 194 | 3-H | 2,6 | Pr | 1R-trans-Z |
| 195 | 3-H | 2,4,6 | Pr | 1R-trans-Z |
| 196 | 3-Br | 4 | Pr | 1R-trans-Z |
| 197 | 3-CHF$_2$ | 2,4,6 | Pr | 1R-trans-Z |
| 198 | 4-allyl | 2,6 | Pr | 1R-trans-Z |
| 199 | 4-allyl | 3,5 | Pr | 1R-trans-Z |
| 200 | 4-H | 2,3,5,6 | Pr | 1R-trans-E |
| 201 | 4-F | 2,3,5,6 | Pr | 1R-trans-E |
| 202 | 4-Me | 2,3,5,6 | Pr | 1R-trans-E |
| 203 | 4-vinyl | 2,3,5,6 | Pr | 1R-trans-E |
| 204 | 4-allyl | 2,3,5,6 | Pr | 1R-trans-E |
| 205 | 4-CF$_3$ | 2,3,5,6 | Pr | 1R-trans-E |
| 206 | 4-MeOCH$_2$ | 2,3,5,6 | Pr | 1R-trans-E |
| 207 | 4-MeO | 2,3,5,6 | Pr | 1R-trans-E |
| 208 | 4-MeS | 2,3,5,6 | Pr | 1R-trans-E |
| 209 | 2-H | 3,4,5,6 | Pr | 1R-trans-E |
| 210 | 2-Me | 3,4,5,6 | Pr | 1R-trans-E |
| 211 | 3-CF$_3$O | 2,4,5,6 | Pr | 1R-trans-E |
| 212 | 2-Cl | 6 | Pr | 1R-trans-E |
| 213 | 2-CF$_3$ | 6 | Pr | 1R-trans-E |
| 214 | 3-H | 2,4 | Pr | 1R-trans-E |
| 215 | 3-H | 2,6 | Pr | 1R-trans-E |
| 216 | 3-H | 2,4,6 | Pr | 1R-trans-E |
| 217 | 3-Br | 4 | Pr | 1R-trans-E |
| 218 | 3-CHF$_2$ | 2,4,6 | Pr | 1R-trans-E |
| 219 | 4-allyl | 2,6 | Pr | 1R-trans-E |
| 220 | 4-allyl | 3,5 | Pr | 1R-trans-E |
| 221 | 4-H | 2,3,5,6 | Pr | 1R-cis-Z |
| 222 | 4-F | 2,3,5,6 | Pr | 1R-cis-Z |
| 223 | 4-Me | 2,3,5,6 | Pr | 1R-cis-Z |
| 224 | 4-vinyl | 2,3,5,6 | Pr | 1R-cis-Z |
| 225 | 4-allyl | 2,3,5,6 | Pr | 1R-cis-Z |
| 226 | 4-CF$_3$ | 2,3,5,6 | Pr | 1R-cis-Z |
| 227 | 4-MeOCH$_2$ | 2,3,5,6 | Pr | 1R-cis-Z |
| 228 | 4-MeO | 2,3,5,6 | Pr | 1R-cis-Z |
| 229 | 4-MeS | 2,3,5,6 | Pr | 1R-cis-Z |
| 230 | 2-H | 3,4,5,6 | Pr | 1R-cis-Z |
| 231 | 2-Me | 3,4,5,6 | Pr | 1R-cis-Z |
| 232 | 3-CF$_3$O | 2,4,5,6 | Pr | 1R-cis-Z |
| 233 | 2-Cl | 6 | Pr | 1R-cis-Z |
| 234 | 2-CF$_3$ | 6 | Pr | 1R-cis-Z |
| 235 | 3-H | 2,4 | Pr | 1R-cis-Z |
| 236 | 3-H | 2,6 | Pr | 1R-cis-Z |
| 237 | 3-H | 2,4,6 | Pr | 1R-cis-Z |
| 238 | 3-Br | 4 | Pr | 1R-cis-Z |
| 239 | 3-CHF$_2$ | 2,4,6 | Pr | 1R-cis-Z |
| 240 | 4-allyl | 2,6 | Pr | 1R-cis-Z |
| 241 | 4-allyl | 3,5 | Pr | 1R-cis-Z |
| 242 | 4-H | 2,3,5,6 | H | 1RS-trans |
| 243 | 4-F | 2,3,5,6 | H | 1RS-trans |
| 244 | 4-Me | 2,3,5,6 | H | 1RS-trans |
| 245 | 4-vinyl | 2,3,5,6 | H | 1RS-trans |
| 246 | 4-allyl | 2,3,5,6 | H | 1RS-trans |
| 247 | 4-CF$_3$ | 2,3,5,6 | H | 1RS-trans |
| 248 | 4-MeOCH$_2$ | 2,3,5,6 | H | 1RS-trans |
| 249 | 4-MeO | 2,3,5,6 | H | 1RS-trans |
| 250 | 4-MeS | 2,3,5,6 | H | 1RS-trans |
| 251 | 2-H | 3,4,5,6 | H | 1RS-trans |
| 252 | 2-Me | 3,4,5,6 | H | 1RS-trans |
| 253 | 3-CF$_3$O | 2,4,5,6 | H | 1RS-trans |
| 254 | 2-Cl | 6 | H | 1RS-trans |
| 255 | 2-CF$_3$ | 6 | H | 1RS-trans |
| 256 | 3-H | 2,4 | H | 1RS-trans |
| 257 | 3-H | 2,6 | H | 1RS-trans |
| 258 | 3-H | 2,4,6 | H | 1RS-trans |
| 259 | 3-Br | 4 | H | 1RS-trans |
| 260 | 3-CHF$_2$ | 2,4,6 | H | 1RS-trans |
| 261 | 4-allyl | 2,6 | H | 1RS-trans |
| 262 | 4-allyl | 3,5 | H | 1RS-trans |
| 263 | 4-H | 2,3,5,6 | H | 1RS-cis |
| 264 | 4-F | 2,3,5,6 | H | 1RS-cis |
| 265 | 4-Me | 2,3,5,6 | H | 1RS-cis |
| 266 | 4-vinyl | 2,3,5,6 | H | 1RS-cis |
| 267 | 4-allyl | 2,3,5,6 | H | 1RS-cis |
| 268 | 4-CF$_3$ | 2,3,5,6 | H | 1RS-cis |
| 269 | 4-MeOCH$_2$ | 2,3,5,6 | H | 1RS-cis |
| 270 | 4-MeO | 2,3,5,6 | H | 1RS-cis |
| 271 | 4-MeS | 2,3,5,6 | H | 1RS-cis |
| 272 | 2-H | 3,4,5,6 | H | 1RS-cis |
| 273 | 2-Me | 3,4,5,6 | H | 1RS-cis |
| 274 | 3-CF$_3$O | 2,4,5,6 | H | 1RS-cis |
| 275 | 2-Cl | 6 | H | 1RS-cis |
| 276 | 2-CF$_3$ | 6 | H | 1RS-cis |
| 277 | 3-H | 2,4 | H | 1RS-cis |
| 278 | 3-H | 2,6 | H | 1RS-cis |
| 279 | 3-H | 2,4,6 | H | 1RS-cis |
| 280 | 3-Br | 4 | H | 1RS-cis |
| 281 | 3-CHF$_2$ | 2,4,6 | H | 1RS-cis |
| 282 | 4-allyl | 2,6 | H | 1RS-cis |
| 283 | 4-allyl | 3,5 | H | 1RS-cis |
| 284 | 4-H | 2,3,5,6 | Me | 1RS-trans-Z |
| 285 | 4-F | 2,3,5,6 | Me | 1RS-trans-Z |
| 286 | 4-Me | 2,3,5,6 | Me | 1RS-trans-Z |
| 287 | 4-vinyl | 2,3,5,6 | Me | 1RS-trans-Z |
| 288 | 4-allyl | 2,3,5,6 | Me | 1RS-trans-Z |
| 289 | 4-CF$_3$ | 2,3,5,6 | Me | 1RS-trans-Z |
| 290 | 4-MeOCH$_2$ | 2,3,5,6 | Me | 1RS-trans-Z |
| 291 | 4-MeO | 2,3,5,6 | Me | 1RS-trans-Z |
| 292 | 4-MeS | 2,3,5,6 | Me | 1RS-trans-Z |
| 293 | 2-H | 3,4,5,6 | Me | 1RS-trans-Z |
| 294 | 2-Me | 3,4,5,6 | Me | 1RS-trans-Z |
| 295 | 3-CF$_3$O | 2,4,5,6 | Me | 1RS-trans-Z |
| 296 | 2-Cl | 6 | Me | 1RS-trans-Z |

TABLE 1-continued

| Compound Nos. | $R^1$ | Position substituted by $F_n$ | X | Isomerism of acid component |
|---|---|---|---|---|
| 297 | 2-$CF_3$ | 6 | Me | 1RS-trans-Z |
| 298 | 3-H | 2,4 | Me | 1RS-trans-Z |
| 299 | 3-H | 2,6 | Me | 1RS-trans-Z |
| 300 | 3-H | 2,4,6 | Me | 1RS-trans-Z |
| 301 | 3-Br | 4 | Me | 1RS-trans-Z |
| 302 | 3-$CHF_2$ | 2,4,6 | Me | 1RS-trans-Z |
| 303 | 4-allyl | 2,6 | Me | 1RS-trans-Z |
| 304 | 4-allyl | 3,5 | Me | 1RS-trans-Z |
| 305 | 4-H | 2,3,5,6 | Me | 1RS-trans-E |
| 306 | 4-F | 2,3,5,6 | Me | 1RS-trans-E |
| 307 | 4-Me | 2,6 | Me | 1RS-trans-E |
| 308 | 4-vinyl | 2,3,5,6 | Me | 1RS-trans-E |
| 309 | 4-allyl | 2,6 | Me | 1RS-trans-E |
| 310 | 4-$CF_3$ | 2,3,5,6 | Me | 1RS-trans-E |
| 311 | 4-$MeOCH_2$ | 2,3,5,6 | Me | 1RS-trans-E |
| 312 | 4-MeO | 2,3,5,6 | Me | 1RS-trans-E |
| 313 | 4-MeS | 2,3,5,6 | Me | 1RS-trans-E |
| 314 | 2-H | 3,4,5,6 | Me | 1RS-trans-E |
| 315 | 2-Me | 3,4,5,6 | Me | 1RS-trans-E |
| 316 | 3-$CF_3O$ | 2,4,5,6 | Me | 1RS-trans-E |
| 317 | 2-Cl | 6 | Me | 1RS-trans-E |
| 318 | 2-$CF_3$ | 6 | Me | 1RS-trans-E |
| 319 | 3-H | 2,4 | Me | 1RS-trans-E |
| 320 | 3-H | 2,6 | Me | 1RS-trans-E |
| 321 | 3-H | 2,4,6 | Me | 1RS-trans-E |
| 322 | 3-Br | 4 | Me | 1RS-trans-E |
| 323 | 3-$CHF_2$ | 2,4,6 | Me | 1RS-trans-E |
| 324 | 4-allyl | 2,6 | Me | 1RS-trans-E |
| 325 | 4-allyl | 3,5 | Me | 1RS-trans-E |
| 326 | 4-H | 2,3,5,6 | Me | 1RS-cis-Z |
| 327 | 4-F | 2,3,5,6 | Me | 1RS-cis-Z |
| 328 | 4-Me | 2,3,5,6 | Me | 1RS-cis-Z |
| 329 | 4-vinyl | 2,3,5,6 | Me | 1RS-cis-Z |
| 330 | 4-allyl | 2,3,5,6 | Me | 1RS-cis-Z |
| 331 | 4-$CF_3$ | 2,3,5,6 | Me | 1RS-cis-Z |
| 332 | 4-$MeOCH_2$ | 2,3,5,6 | Me | 1RS-cis-Z |
| 333 | 4-MeO | 2,3,5,6 | Me | 1RS-cis-Z |
| 334 | 4-MeS | 2,3,5,6 | Me | 1RS-cis-Z |
| 335 | 2-H | 3,4,5,6 | Me | 1RS-cis-Z |
| 336 | 2-Me | 3,4,5,6 | Me | 1RS-cis-Z |
| 337 | 3-$CF_3O$ | 2,4,5,6 | Me | 1RS-cis-Z |
| 338 | 2-Cl | 6 | Me | 1RS-cis-Z |
| 339 | 2-$CF_3$ | 6 | Me | 1RS-cis-Z |
| 340 | 3-H | 2,4 | Me | 1RS-cis-Z |
| 341 | 3-H | 2,6 | Me | 1RS-cis-Z |
| 342 | 3-H | 2,4,6 | Me | 1RS-cis-Z |
| 343 | 3-Br | 4 | Me | 1RS-cis-Z |
| 344 | 3-$CHF_2$ | 2,4,6 | Me | 1RS-cis-Z |
| 345 | 4-allyl | 2,6 | Me | 1RS-cis-Z |
| 346 | 4-allyl | 3,5 | Me | 1RS-cis-Z |
| 347 | 4-H | 2,3,5,6 | Et | 1RS-trans-Z |
| 348 | 4-F | 2,3,5,6 | Et | 1RS-trans-Z |
| 349 | 4-Me | 2,3,5,6 | Et | 1RS-trans-Z |
| 350 | 4-vinyl | 2,3,5,6 | Et | 1RS-trans-Z |
| 351 | 4-allyl | 2,3,5,6 | Et | 1RS-trans-Z |
| 352 | 4-$CF_3$ | 2,3,5,6 | Et | 1RS-trans-Z |
| 353 | 4-$MeOCH_2$ | 2,3,5,6 | Et | 1RS-trans-Z |
| 354 | 4-MeO | 2,3,5,6 | Et | 1RS-trans-Z |
| 355 | 4-MeS | 2,3,5,6 | Et | 1RS-trans-Z |
| 356 | 2-H | 3,4,5,6 | Et | 1RS-trans-Z |
| 357 | 2-Me | 3,4,5,6 | Et | 1RS-trans-Z |
| 358 | 3-$CF_3O$ | 2,4,5,6 | Et | 1RS-trans-Z |
| 359 | 2-Cl | 6 | Et | 1RS-trans-Z |
| 360 | 2-$CF_3$ | 6 | Et | 1RS-trans-Z |
| 361 | 3-H | 2,4 | Et | 1RS-trans-Z |
| 362 | 3-H | 2,6 | Et | 1RS-trans-Z |
| 363 | 3-H | 2,4,6 | Et | 1RS-trans-Z |
| 364 | 3-Br | 4 | Et | 1RS-trans-Z |
| 365 | 3-$CHF_2$ | 2,4,6 | Et | 1RS-trans-Z |
| 366 | 4-allyl | 2,6 | Et | 1RS-trans-Z |
| 367 | 4-allyl | 3,5 | Et | 1RS-trans-Z |
| 368 | 4-H | 2,3,5,6 | Et | 1RS-trans-E |
| 369 | 4-F | 2,3,5,6 | Et | 1RS-trans-E |
| 370 | 4-Me | 2,3,5,6 | Et | 1RS-trans-E |
| 371 | 4-vinyl | 2,3,5,6 | Et | 1RS-trans-E |
| 372 | 4-allyl | 2,3,5,6 | Et | 1RS-trans-E |
| 373 | 4-$CF_3$ | 2,3,5,6 | Et | 1RS-trans-E |
| 374 | 4-$MeOCH_2$ | 2,3,5,6 | Et | 1RS-trans-E |
| 375 | 4-MeO | 2,3,5,6 | Et | 1RS-trans-E |
| 376 | 4-MeS | 2,3,5,6 | Et | 1RS-trans-E |
| 377 | 2-H | 3,4,5,6 | Et | 1RS-trans-E |
| 378 | 2-Me | 3,4,5,6 | Et | 1RS-trans-E |
| 379 | 3-$CF_3O$ | 2,4,5,6 | Et | 1RS-trans-E |
| 380 | 2-Cl | 6 | Et | 1RS-trans-E |
| 381 | 2-$CF_3$ | 6 | Et | 1RS-trans-E |
| 382 | 3-H | 2,4 | Et | 1RS-trans-E |
| 383 | 3-H | 2,6 | Et | 1RS-trans-E |
| 384 | 3-H | 2,4,6 | Et | 1RS-trans-E |
| 385 | 3-Br | 4 | Et | 1RS-trans-E |
| 386 | 3-$CHF_2$ | 2,4,6 | Et | 1RS-trans-E |
| 387 | 4-allyl | 2,6 | Et | 1RS-trans-E |
| 388 | 4-allyl | 3,5 | Et | 1RS-trans-E |
| 389 | 4-H | 2,3,5,6 | Et | 1RS-cis-Z |
| 390 | 4-F | 2,3,5,6 | Et | 1RS-cis-Z |
| 391 | 4-Me | 2,3,5,6 | Et | 1RS-cis-Z |
| 392 | 4-vinyl | 2,3,5,6 | Et | 1RS-cis-Z |
| 393 | 4-allyl | 2,3,5,6 | Et | 1RS-cis-Z |
| 394 | 4-$CF_3$ | 2,3,5,6 | Et | 1RS-cis-Z |
| 395 | 4-$MeOCH_2$ | 2,3,5,6 | Et | 1RS-cis-Z |
| 396 | 4-MeO | 2,3,5,6 | Et | 1RS-cis-Z |
| 397 | 4-MeS | 2,3,5,6 | Et | 1RS-cis-Z |
| 398 | 2-H | 3,4,5,6 | Et | 1RS-cis-Z |
| 399 | 2-Me | 3,4,5,6 | Et | 1RS-cis-Z |
| 400 | 3-$CF_3O$ | 2,4,5,6 | Et | 1RS-cis-Z |
| 401 | 2-Cl | 6 | Et | 1RS-cis-Z |
| 402 | 2-$CF_3$ | 6 | Et | 1RS-cis-Z |
| 403 | 3-H | 2,4 | Et | 1RS-cis-Z |
| 404 | 3-H | 2,6 | Et | 1RS-cis-Z |
| 405 | 3-H | 2,4,6 | Et | 1RS-cis-Z |
| 406 | 3-Br | 4 | Et | 1RS-cis-Z |
| 407 | 3-$CHF_2$ | 2,4,6 | Et | 1RS-cis-Z |
| 408 | 4-allyl | 2,6 | Et | 1RS-cis-Z |
| 409 | 4-allyl | 3,5 | Et | 1RS-cis-Z |
| 410 | 4-H | 2,3,5,6 | Pr | 1RS-trans-Z |
| 411 | 4-F | 2,3,5,6 | Pr | 1RS-trans-Z |
| 412 | 4-Me | 2,3,5,6 | Pr | 1RS-trans-Z |
| 413 | 4-vinyl | 2,3,5,6 | Pr | 1RS-trans-Z |
| 414 | 4-allyl | 2,3,5,6 | Pr | 1RS-trans-Z |
| 415 | 4-$CF_3$ | 2,3,5,6 | Pr | 1RS-trans-Z |
| 416 | 4-$MeOCH_2$ | 2,3,5,6 | Pr | 1RS-trans-Z |
| 417 | 4-MeO | 2,3,5,6 | Pr | 1RS-trans-Z |
| 418 | 4-MeS | 2,3,5,6 | Pr | 1RS-trans-Z |
| 419 | 2-H | 3,4,5,6 | Pr | 1RS-trans-Z |
| 420 | 2-Me | 3,4,5,6 | Pr | 1RS-trans-Z |
| 421 | 3-$CF_3O$ | 2,4,5,6 | Pr | 1RS-trans-Z |
| 422 | 2-Cl | 6 | Pr | 1RS-trans-Z |
| 423 | 2-$CF_3$ | 6 | Pr | 1RS-trans-Z |
| 424 | 3-H | 2,4 | Pr | 1RS-trans-Z |
| 425 | 3-H | 2,6 | Pr | 1RS-trans-Z |
| 426 | 3-H | 2,4,6 | Pr | 1RS-trans-Z |
| 427 | 3-Br | 4 | Pr | 1RS-trans-Z |
| 428 | 3-$CHF_2$ | 2,4,6 | Pr | 1RS-trans-Z |
| 429 | 4-allyl | 2,6 | Pr | 1RS-trans-Z |
| 430 | 4-allyl | 3,5 | Pr | 1RS-trans-Z |
| 431 | 4-H | 2,3,5,6 | Pr | 1RS-trans-E |
| 432 | 4-F | 2,3,5,6 | Pr | 1RS-trans-E |
| 433 | 4-Me | 2,3,5,6 | Pr | 1RS-trans-E |
| 434 | 4-vinyl | 2,3,5,6 | Pr | 1RS-trans-E |
| 435 | 4-allyl | 2,3,5,6 | Pr | 1RS-trans-E |
| 436 | 4-$CF_3$ | 2,3,5,6 | Pr | 1RS-trans-E |
| 437 | 4-$MeOCH_2$ | 2,3,5,6 | Pr | 1RS-trans-E |
| 438 | 4-MeO | 2,3,5,6 | Pr | 1RS-trans-E |
| 439 | 4-MeS | 2,3,5,6 | Pr | 1RS-trans-E |
| 440 | 2-H | 3,4,5,6 | Pr | 1RS-trans-E |
| 441 | 2-Me | 3,4,5,6 | Pr | 1RS-trans-E |
| 442 | 3-$CF_3O$ | 2,4,5,6 | Pr | 1RS-trans-E |
| 443 | 2-Cl | 6 | Pr | 1RS-trans-E |
| 444 | 2-$CF_3$ | 6 | Pr | 1RS-trans-E |
| 445 | 3-H | 2,4 | Pr | 1RS-trans-E |
| 446 | 3-H | 2,6 | Pr | 1RS-trans-E |
| 447 | 3-H | 2,4,6 | Pr | 1RS-trans-E |
| 448 | 3-Br | 4 | Pr | 1RS-trans-E |

TABLE 1-continued

| Compound Nos. | $R^1$ | Position substituted by $F_n$ | X | Isomerism of acid component |
|---|---|---|---|---|
| 449 | 3-CHF$_2$ | 2,4,6 | Pr | 1RS-trans-E |
| 450 | 4-allyl | 2,6 | Pr | 1RS-trans-E |
| 451 | 4-allyl | 3,5 | Pr | 1RS-trans-E |
| 452 | 4-H | 2,3,5,6 | Pr | 1RS-cis-Z |
| 453 | 4-F | 2,3,5,6 | Pr | 1RS-cis-Z |
| 454 | 4-Me | 2,3,5,6 | Pr | 1RS-cis-Z |
| 455 | 4-vinyl | 2,3,5,6 | Pr | 1RS-cis-Z |
| 456 | 4-allyl | 2,3,5,6 | Pr | 1RS-cis-Z |
| 457 | 4-CF$_3$ | 2,3,5,6 | Pr | 1RS-cis-Z |
| 458 | 4-MeOCH$_2$ | 2,3,5,6 | Pr | 1RS-cis-Z |
| 459 | 4-MeO | 2,3,5,6 | Pr | 1RS-cis-Z |
| 460 | 4-MeS | 2,3,5,6 | Pr | 1RS-cis-Z |
| 461 | 2-H | 3,4,5,6 | Pr | 1RS-cis-Z |
| 462 | 2-Me | 3,4,5,6 | Pr | 1RS-cis-Z |
| 463 | 3-CF$_3$ | 2,4,5,6 | Pr | 1RS-cis-Z |
| 464 | 2-Cl | 6 | Pr | 1RS-cis-Z |
| 465 | 2-CF$_3$ | 6 | Pr | 1RS-cis-Z |
| 466 | 3-H | 2,4 | Pr | 1RS-cis-Z |
| 467 | 3-H | 2,6 | Pr | 1RS-cis-Z |
| 468 | 3-H | 2,4,6 | Pr | 1RS-cis-Z |
| 469 | 3-Br | 4 | Pr | 1RS-cis-Z |
| 470 | 3-CHF$_2$ | 2,4,6 | Pr | 1RS-cis-Z |
| 471 | 4-allyl | 2,6 | Pr | 1RS-cis-Z |
| 472 | 4-allyl | 3,5 | Pr | 1RS-cis-Z |

The physical property values of the present compounds are shown below.

Present compound 4 $^1$H-NMR (CDCl$_3$, TMS) δ 1.15(3H, s), 1.28(3H,s), 1.45(3H,d,J=5.4), 1.70(3H,dd,J=6.8,1.7), 2.18(1H, brdd,J=8.4,5.4), 5.11(1H,ddq,J=10.6,8.4,1.7), 5.21 (1H,brs), 5.60(1H,dqd,J=10.6,7.0,1.2)

Present compound 5 $^1$H-NMR (CDCl$_3$, TMS) δ 1.13(3H, s), 1.24(3H,s), 1.48(3H,d,J=5.4), 1.68(3H,dd,J=6.6,1.4), 2.03(1H, brdd,J=8.2,5.4), 3.48(2H,dt,J=6.3,1.3), 5.07–5.24 (5H,m), 5.62(1H,dq,J=15.1,6.5), 5.89(1H,ddt,J=16.7,10.3, 6.3)

Present compound 6 $^1$H-NMR (CDCl$_3$, TMS) δ 1.14(3H, s), 1.28(3H,s), 1.45(1H,d,J=5.4), 1.70(3H,dd,J=6.9,1.7), 2.18(1H, brdd,J=8.4,5.4),4.10(3H,t,J=1.4),5.11(1H,ddq, J=10.5,8.4,1.7), 5.18(1H,t,J=1.6), 5.19(1H,t,J=1.6), 5.60 (1H, dqd,J=10.5, 7.1,1.4)

Present compound 7 $^1$H-NMR (CDCl$_3$, TMS) δ 0.98(3H, t,J=7.5), 1.13(3H,s), 1.27(3H,s), 1.45(1H,d,J=5.3), 2.07–2.18(3H,m), 2.28(3H,t,J=2.2), 5.05(1H,ddt,J=10.6,8.6, 1.5), 5.20(1H,t, J=1.4), 5.21(1H,t,J=1.4), 5.52(1H,dqd,J= 10.6,7.3,1.1)

Present compound 8 n$_D^{25}$ 1.4558 (refractive index)

Present compound 9 n$_D^{21}$ 1.4810 (refractive index)

Present compound 10 $^1$H-NMR (CDCl$_3$, TMS) δ 1.20 (3H,s), 1.27(3H,s), 1.67–1.74(4H,m), 1.98(1H,t,J=8.0), 5.25 (2H,s,J=2.0), 5.60–5.80(2H,m) 7.05(1H,t,J=8.6), 7.20–7.30 (2H,m)

Next, formulation examples are described below. Parts represent parts by weight and the present compounds are shown by the compound numbers in table 1.

Formulation Example 1
Emulusifiable Concentrates

Ten parts of each of the present compounds 1–472 are dissolves in a mixture of 35 parts of xylene and 35 parts of dimethylformamide, mixed with 14 parts of polyoxyethylenestyryl phenyl ether and 6 parts of calcium dodecylbenzenesulfonate, and stirred sufficiently to give 10% emulusifiable concentrates for each compound.

Formulation Example 2
Wettable Powders

Twenty parts of each of the present compounds 1–472 are added to a mixture of 4 parts of sodium laurylsulfate, 2 parts of calcium ligninsulfonate, 20 parts of fine powder of synthetic hydrated silica and 54 parts of diatomaceous earth and then stirred with a blender to give 20% wettable powders for each compound.

Formulation Example 3
Granules

Five parts of each of the present compounds 1–472 are mixed with 5 parts of fine powder of synthetic hydrated silica, 5 parts of sodium dodecylbenzenesulfonate, 30 parts of bentonite and 55 parts of clay and stirred. Then, a proper amount of water is added to the mixture, which is stirred, granulated and dried by air to give 5% granules for each compound.

Formulation Example 4
Dusts

One part of each of the present compounds 1–472 is dissolved in a proper amount of acetone and mixed with 5 parts of fine powder of synthetic hydrated silica, 0.3 part of PAP and 93.7 parts of clay, stirred with a blender and dried by air to give 1% dusts for each compound.

Formulation Example 5
Flowable Formulation

A mixture of 20 parts of each of the present compounds 1–472, 1.5 parts of sorbitan trioleate and 28.5 parts of aqueous solution containing 2 parts of polyvinyl alcohol is pulverized by sand-grinder (particle diameter : 3μ or less). Then, 40 parts of aqueous solution, containing 0.05 part of xanthan gum and 0.1 part of aluminum magnesium silicate, and 10 parts of propylene glycol are added to the mixture and stirred to give a 20% flowable formulation for each compound.

Formulation Example 6
Oil Solution 0.1 part of each of the present compounds 1–472 is dissolved in 5 parts of xylene and 5 parts of trichloroethane and mixed with 89.9 parts of deodorized kerosene to give a 0.1% oil solution for each compound.

Formulation Example 7
Oil-based Aerosol

An aerosol vessel is filled with the solution obtained by dissolving 1 part of each of the present compounds 1–472 with 5 parts of dichloromethane and 34 parts of deodorized kerosene. The vessel is then equipped with a valve and 60 parts of propellant (liquefied petroleum gas) is charged through the valve into the aerosol vessel under pressure to give an oil-based aerosol for each compound.

Formulation Example 8
Water-based Aerosols

An aerosol vessel is filled with 50 parts of purified water and a mixture of 0.6 part of each of the present compounds 1–472, 5 parts of xylene, 3.4 parts of deodorized kerosene and 1 part of emulsifier (Atmos 300; trademark of Atlas Chemical Co.). The vessel is then equipped with a valve and 40 parts of propellant (liquefied petroleum gas) are charged through a valve into the aerosol vessel under pressure to give a water-based aerosol for each compound.

Formulation Example 9
Mosquito-coil

A solution prepared by dissolving 0.3 g of each of the present compounds 1–472 in 20 ml of acetone is homogeneously mixed with 99.7 g of a carrier for amosquito-coil (mixture of Tabu powder, Pyrethrum marc and wood powder at the ratio of 4:3:3). After 120 ml of water is added, the mixture is kneaded sufficiently, molded and dried to give a mosquito-coil for each compound.

Formulation Example 10
Mosquito-mat For Electric Heating Fumigation

Ten mililiters (10 ml) of solution is prepared by dissolving 0.8 g of each of the present compounds 1–472 and 0.4 g of piperonyl butoxide in acetone. 0.5 ml of the obtained solution is impregnated with a base material (a plate of compacted fibrils of a mixture of pulp and cotton linters: 2.5 cm×1.5 cm, thickness 0.3 cm) homogeneously to give a mosquito-mat for each compound.

Formulation Example 11
Solution For Electric Heating Fumigation

Three parts of each of the present compounds 1–472 is dissolved in 97 parts of deodorized kerosene. The obtained solution is charged in a vessel of polyvinyl chloride. In the vessel is inserted a porous absorptive wick which is inorganic powder solidified with a binder and then calcined, the upper portion of which wick can be heated with a heater, to give electric heating fumigation devices using a liquid for each compound.

Formulation Example 12
Fumigant

A solution prepared by dissolving 100 mg of each of the present compounds 1–472 in an appropriate amount of acetone is impregnated with a porous ceramic plate (4.0 cm×4.0 cm, thickness 1.2 cm) to give a fumigant for each compound.

Formulation Example 13
Poison Bait

A solution prepared by dissolving 10 mg of each of the present compounds 1–472 in 0.5 ml of acetone is mixed with 5 g of solid feed powder for animals (solid feed powder for breeding: CE-2 manufactured by Japan Kurea Co., Ltd.). Then acetone was removed by air drying to obtain a 0.2% poison bait for each compound.

Formulation Example 14
Acaricidal Sheet

An acetone solution containing each of the present compounds 1–472 is impregnated filter paper so that the concentration of the present compound is 1 g/1 m$^2$ and the acetone is removed by air drying to give an acaricidal sheet for each compound.

Formulation Example 15
Volatile Agent For Use at Room Temperature

A solution prepared by dissolving 100 μg of each of the present compounds 1–472 in an appropriate amount of acetone is applied onto filter paper (2.0 cm×2.0 cm, thickness 0.3 mm) and the acetone is removed by air drying to give a volatile agent for each compound.

Formulation Example 16
Volatile Agent For Use at Room Temperature

A solution prepared by dissolving 100 μg of each of the present compounds 1–472 in 20 ml of acetone is applied onto filter paper (20 cm×50 cm) and the acetone is removed by air drying to give a volatile agent for each compound.

Formulation Example 17
Microcapsulated Formulation

A mixture of 10 parts of each of the present compounds 1–472, 10 parts of phenylxylylethane and 0.5 part of Sumidur L-75 (tolylenediisocyanate manufactured by Sumitomo Bayer Urethane Co., Ltd.) is added to 20 parts of a 10% aqueous solution of gum arabic, and stirred with a homomixer to give an emulsion having the mean particle diameter of 20 μm. The emulsion is further mixed with 2 parts of ethylene glycol and allowed to react on a water bath of 60° C. for 24 hours to give a microcapsule slurry.

A thicking agent is prepared by dispersing 0.2 part of xanthan gum and 1.0 part of Beagum R (aluminum magnesium silicate manufactured by Sanyo Chemical Co., Ltd.) in 56.3 parts of ion-exchanged water.

42.5 parts of the above microcapsule slurry and 57.5 parts of the above thicking agent are mixed to give a 10% microencapsulated formulation for each compound.

The following test examples demonstrate that the present compounds are useful as active ingredients of pesticides. (4-allylphenyl)methyl 1RS-trans-2,2-dimethyl-3-((E)-1-propenyl)cyclopropanecarboxylate (hereinafter referred as "Reference Compound A") described in JP-sho-47-43333A and (2,3,5,6-tetrafluorophenyl)methyl(1R)-trans-2,2-dimethyl-3-(2-methyl-1-propenyl)cyclopropanecarboxylate (hereinafter referred as "Reference Compound B") described in JP-hei-5-32509A are used for comparison. The present compounds are designated by their compound numbers described in Table 1 and the reference compounds are designated by their compound symbols.

Biological Test 1
Insecticidal Test Against Tobacco Cutworm

Flowable formulations of each of the present compounds 1 to 10 obtained according to the formulation example 5 were diluted with water to be 500 ppm concentration of each of the active ingredient. Two mililiters (2 mL) of the dilution were impregnated with 13 g of artificial bait (Insecta LF manufactured by Nippon Nosan kogyo Co.) in a polyethylene cup (diameter: 11 cm). Five fourth-instar larvae of tobacco cutworms (*Spodoptera litura*) were put in the cup and the mortality of the larvae was examined after 6 days. As a result, it was found that the present compounds 1 to 10 exhibited the mortality of 100%.

Biological Test 2
Insecticidal Test Against Cotton Aphid

A cucumber in a first-leaf stage was inoculated with a leaf piece lived in by cotton aphids (*Aphis gossypii*) in a polyethylene cup. After one day, a 500 ppm aqueous dilution of each flowable formulation of the present compounds 1, 4, 5, 7 and 10 obtained according to the formulation example 5 was applied at a rate of 20 mL per pot. Controlling values were calculated by the formula below in 6 days after application of the dilution.

$$\text{Controlling value} = \{1 - (Cb \times Tai)/(Tb \times Cai)\} \times 100$$

Cb: Number of insects before application in non-treated area

Cai: Number of insects observed in non-treated area

Tb: Number of insects before application in treated area

Tai: Number of insects observed in treated area

As a result, it was found that the present compounds 1, 4, 5, 7 and 10 exhibited the controlling values of 90 or more.

Biological Test 3

Insecticidal Test Against Housefly

Filter paper of 5.5 cm in diameter was laid in the bottom of a polyethylene cup (diameter: 5.5 cm). After 0.7 ml of each 500 ppm aqueous dilution obtained by diluting flowable formulation of the present compounds 1, 2, 3, 4, 5, 6, 7, 9 and reference compound A prepared according to the formulation example 5 was dropped on the filter paper and 30 mg of sucrose as bait was uniformly scattered. Ten female adult houseflies (Musca domestica) were left in the cup with a cover. After 24 hours, the mortality was examined. As a result, it was found that the present compounds 1, 2, 3, 4, 5, 6, 7 and 9 exhibited the mortality of 100%. In contrast, reference compound A gave 40% or less of the mortality.

Biological Test 4

Insecticidal Test Against German Cockroach

Filter paper of 5.5 cm in diameter was laid in the bottom of a polyethylene cup (diameter: 5.5 cm). After 0.7 ml of a 500 ppm aqueous dilution obtained by diluting flowable formulation of the present compounds 1, 2, 3, 4, 5, 6, 7, 9 and reference compound A prepared according to the formulation example 5 was dropped on the filter paper and approximately 30 mg of sucrose as bait was uniformly scattered. Two male German cockroaches (Blattella germanica) were left in the cup with a cover. After six days, the mortality was examined. As a result, it was found that the present compounds 1, 2, 3, 4, 5, 6, 7 and 9 exhibited the mortality of 100%. In contrast, reference compound A gave 50% or less of the mortality.

Biological Test 5

Insecticidal Test Against Common Mosquito 0.7 ml of aqueous dilution, obtained by diluting flowable formulation prepared for the present compounds 1–10 according to the formulation example 5, was added to 100 ml of ion-exchanged water (concentration of active ingredient: 3.5 ppm). Twenty last-instar larvae of common mosquitoes (Culex pipiens pallens) were left in the water. After one day, the mortality of the common mosquitoes was examined. As a result, it was found that the present compounds 1–10 exhibited the mortality of 100%.

Biological Test 6

Insecticidal Test Against Webbing Clothes Moth (Volatilation at Room Temperature)

A wool muslin fabric (2 cm×2 cm in size) was placed on the bottom of a polyethylene cup (bottom diameter: 10 cm, opening part diameter: 12.5 cm, height: 9.5 cm, volume: 950 cm³). Ten middle instar larvae of webbing clothes moth (Tineola bisselliella) were put in the cup, the cup was covered up and the volatile agent of the present compounds 1–9 and reference compound A prepared according to the formulation example 15 was hung from the cap in the interior of the cup. After standing at 25° C. for 1 week, the cup was opened, and the percent moribund and the degree of damage of the wool muslin fabric by the moths were examined.

The damage was evaluated as follows:

+++: severe damage

++: heavy damage

+: slight damage

±: rare damage

−: no damage

The results are shown in table 2.

TABLE 2

| Compounds | Percent moribund (%) | Damage |
|---|---|---|
| 1 | 100 | − |
| 2 | 100 | − |
| 3 | 100 | − |
| 4 | 100 | − |
| 5 | 100 | − |
| 6 | 100 | − |
| 7 | 100 | − |
| 8 | 100 | − |
| 9 | 100 | − |
| Reference Compound A | 10 | +++ |

Biological Test 7

Insecticidal Test Against Common Mosquito

In the center of a 28 m³ test chamber(4.3 m×2.65 m×height: 2.45 m), each volatile agent of the present compounds 1, 2, 4, 6 and reference compound B prepared according to the formulation example 16 was hung and set the upper end of the volatile agent 1.7 m in height and set its lower end 1.2 m in height from the flour. Four nylon-net cages (cylindrical, 30 cm in diameter and 20 cm in height) with each 20 female common mosquitoes (Culex pipiens pallens) were hung and set the lower end 60 cm in height, detached 60 cm horizontally from the volatile agent in four directions. After 60 minutes, the number of knocked down mosquitoes was counted and the percentage was calculated. In order to stir the air in the chamber, a fan was set under the volatile agent and a board was set between the fan and the volatile agent for preventing the fan from blowing the volatile agent directly in this test. The results were shown in table 3.

TABLE 3

| Compounds | Knocked-down Percent (%) |
|---|---|
| 1 | 94 |
| 2 | 60 |
| 4 | 99 |
| 6 | 70 |
| Reference Compound B | 29 |

What is claimed is:

1. An ester compound shown by the formula (I):

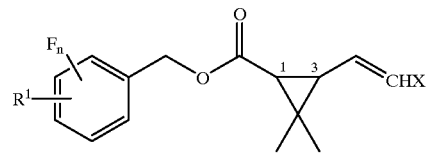

wherein $R^1$ represents a hydrogen atom, halogen atom, $C_1$–$C_3$ alkyl group optionally substituted by halogen atom(s), $C_2$–$C_3$ alkenyl group optionally substituted by halogen atom(s), $C_1$–$C_3$ alkoxy group optionally substituted by halogen atom(s), $C_1$–$C_3$ alkylthio group optionally substituted by halogen atom(s) or ($C_1$–$C_3$ alkoxy)methyl group optionally substituted by halogen atom(s), n represents an integer of 1 to 4 and X represents a hydrogen atom or $C_1$–$C_3$ alkyl group.

2. An ester compound according to claim 1, wherein 1-position of the cyclopropane ring shown by the formula (I) has an R-configuration.

3. An ester compound according to claim 1 or 2, wherein the isomerism of the substituents at 1-position and 3-position of the cyclopropane ring shown by the formula (I) is trans.

4. An ester compound according to claim 1 or 2, wherein the isomerism of the substituents at 1-position and 3-position of the cyclopropane ring shown by the formula (I) is cis.

5. An ester compound according to claim 1, wherein $R^1$ in the formula (I) is a hydrogen atom.

6. An ester compound according to claim 1, wherein $R^1$ in the formula (I) is a methyl group.

7. An ester compound according to claim 1, wherein X in the formula (I) is a methyl group.

8. A ester compound according to claim 1, which is (2,3,5,6-tetrafluoro-4-methylphenyl)methyl 2,2-dimethyl-3-(1-propenyl)cyclopropanecarboxylate.

9. A ester compound according to claim 1, which is (2,3,5,6-tetrafluoro-4-methylphenyl)methyl(1R)-trans-2,2-dimethyl-3-((Z)-1-propenyl)cyclopropanecarboxylate.

10. A ester compound according to claim 1, which is (2,3,5,6-tetrafluorophenyl)methyl 2,2-dimethyl-3-(1-propenyl)cyclopropanecarboxylate.

11. A ester compound according to claim 1, which is (2,3,5,6-tetrafluorophenyl)methyl(1R)-trans-2,2-dimethyl-3-((Z)-1-propenyl)cyclopropanecarboxylate.

12. A ester compound according to claim 1, which is (2,3,5,6-tetrafluoro-4-methoxyphenyl)methyl 2,2-dimethyl-3-(1-propenyl)cyclopropanecarboxylate.

13. A ester compound according to claim 1, which is (2,3,5,6-tetrafluoro-4-methoxyphenyl)methyl(1R)-trans-2,2-dimethyl-3-((Z)-1-propenyl)cyclopropanecarboxylate.

14. A ester compound according to claim 1, which is (2,3,5,6-tetrafluoro-4-methoxymethylphenyl)methyl 2,2-dimethyl-3-(1-propenyl)cyclopropanecarboxylate.

15. A ester compound according to claim 1, which is (2,3,5,6-tetrafluoro-4-methoxymethylphenyl)methyl(1R)-trans-2,2-dimethyl-3-((Z)-1-propenyl)cyclopropanecarboxylate.

16. A ester compound according to claim 1, which is (2,3,4,5,6-pentafluorophenyl)methyl 2,2-dimethyl-3-(1-propenyl)cyclopropanecarboxylate.

17. A ester compound according to claim 1, which is (2,3,4,5,6-pentafluorophenyl)methyl(1R)-trans-2,2-dimethyl-3-((Z)-1-propenyl)cyclopropanecarboxylate.

18. A pesticidal composition which comprises an ester compound shown by the formula (I):

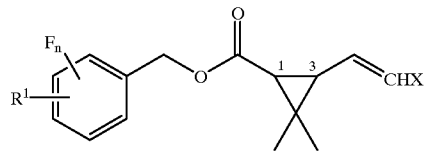

wherein $R^1$ represents a hydrogen atom, halogen atom, $C_1$–$C_3$ alkyl group optionally substituted by halogen atom(s), $C_2$–$C_3$ alkenyl group optionally substituted by halogen atom(s), $C_1$–$C_3$ alkoxy group optionally substituted by halogen atom(s), $C_1$–$C_3$ alkylthio group optionally substituted by halogen atom(s) or ($C_1$–$C_3$ alkoxy)methyl group optionally substituted by halogen atom(s), n represents an integer of 1 to 4 and X represents a hydrogen atom or $C_1$–$C_3$ alkyl group, as an active ingredient, and a carrier.

19. A method for controlling pests which comprises applying an effective amount of an ester compound shown by the formula (I):

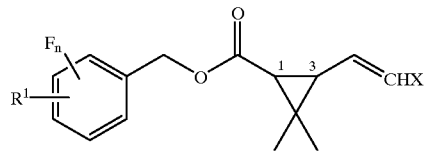

wherein $R^1$ represents a hydrogen atom, halogen atom, $C_1$–$C_3$ alkyl group optionally substituted by halogen atom(s), $C_2$–$C_3$ alkenyl group optionally substituted by halogen atom(s), $C_1$–$C_3$ alkoxy group optionally substituted by halogen atom(s), $C_1$–$C_3$ alkylthio group optionally substituted by halogen atom(s) or ($C_1$–$C_3$ alkoxy)methyl group optionally substituted by halogen atom(s), n represents an integer of 1 to 4 and X represents a hydrogen atom or $C_1$–$C_3$ alkyl group, to pests or locus where pests inhabit.

* * * * *